(12) United States Patent
Lin et al.

(10) Patent No.: US 9,833,537 B2
(45) Date of Patent: Dec. 5, 2017

(54) CALCIUM-BASED BONE CEMENT FORMULA WITH ENHANCED NON-DISPERSIVE ABILITY

(75) Inventors: Jiin-Huey Chern Lin, Winnetka, IL (US); Chien-Ping Ju, Kansas City, MO (US)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 1224 days.

(21) Appl. No.: 13/339,704

(22) Filed: Dec. 29, 2011

(65) Prior Publication Data
US 2013/0138114 A1 May 30, 2013

(30) Foreign Application Priority Data
Nov. 28, 2011 (TW) .............................. 100143476 A

(51) Int. Cl.
*A61L 27/42* (2006.01)
*A61L 24/00* (2006.01)

(52) U.S. Cl.
CPC .......... *A61L 24/0063* (2013.01); *A61L 27/425* (2013.01); *A61L 2400/06* (2013.01); *A61L 2430/02* (2013.01)

(58) Field of Classification Search
USPC ....................................................... 523/116
See application file for complete search history.

(56) References Cited

U.S. PATENT DOCUMENTS

| 4,684,673 A | * | 8/1987 | Adachi ............... A61L 24/0084 523/113 |
| 5,149,368 A | * | 9/1992 | Liu ........................ A61K 6/033 106/35 |
| 5,281,265 A | * | 1/1994 | Liu ...................... A61K 6/0625 106/157.5 |
| 6,616,742 B2 | * | 9/2003 | Lin ...................... A61K 6/0085 106/35 |
| 9,125,966 B2 | * | 9/2015 | Bohner ............... A61L 24/0063 |
| 2002/0073894 A1 | * | 6/2002 | Genge .................. A61K 6/033 106/35 |
| 2007/0092856 A1 | * | 4/2007 | Chow ................. A61K 6/0038 433/228.1 |
| 2008/0182920 A1 | * | 7/2008 | Towler .................... A61L 27/10 523/116 |
| 2011/0160322 A1 | * | 6/2011 | Huang ............... A61L 24/0036 521/84.1 |

FOREIGN PATENT DOCUMENTS

WO    WO 2008/117043    * 10/2008

OTHER PUBLICATIONS

Polyacrylic acid in Catalog of Aldrich (Sigma-Aldrich) Company. 2015.*

* cited by examiner

*Primary Examiner* — Tae H Yoon
(74) *Attorney, Agent, or Firm* — Bacon & Thomas, PLLC

(57) ABSTRACT

A calcium-based bone cement formula having a powder component and a setting liquid component with a liquid to powder ratio of 0.20 ml/g to 0.50 ml/g is provided, wherein the powder component includes tetracalcium phosphate. The bone cement formula further contains, based on the total weight of the bone cement formula, 0.01-1% of poly(acrylic acid) having a repeating unit of $-(CH_2-C(COOH)H)n-$, wherein n=50-50000.

6 Claims, 2 Drawing Sheets

(a)

(b)

(a)

(b)

(a) (b)

(a) (b)

CALCIUM-BASED BONE CEMENT FORMULA WITH ENHANCED NON-DISPERSIVE ABILITY

FIELD OF THE INVENTION

The exemplary embodiment(s) of the present invention relates to bone repairing substance for medicaments. More specifically, the exemplary embodiment(s) of the present invention relates to a bone cement formula.

BACKGROUND OF THE INVENTION

Bone cement compositions are widely used in bonding, filling, and/or repairing damaged natural bone. Bone cement is typically used in orthopedic, dental procedures, and/or other medical applications.

The applicant of the present application in U.S. patent application Ser. No. 12/907,091, filed 19 Oct. 2010, discloses a bone cement formula having a powder component and a setting liquid component, wherein the powder component includes a calcium sulfate source and a calcium phosphate source with a weight ratio of the calcium sulfate source less than 65%, based on the total weight of the calcium sulfate source and the calcium phosphate source, and the setting liquid component comprises ammonium ion ($NH_4^+$) in a concentration of about 0.5 M to 4 M, wherein the calcium phosphate source includes tetracalcium phosphate (TTCP) and dicalcium phosphate in a molar ratio of TTCP to dicalcium phosphate of about 0.5 to about 2.5, and the calcium sulfate source is calcium sulfate hemihydrate (CSH), calcium sulfate dehydrate (CSD), or anhydrous calcium sulfate. The disclosure of the U.S. patent application Ser. No. 12/907,091 is incorporated herein by reference.

For a minimally invasive procedure of injecting a cement paste into a bone cavity, a thin, long tube is usually used for the transportation of the paste. To more easily deliver the paste through such long, thin tube, use of a less viscous (more dilute or higher L/P ratio) paste has its inherent advantages. However, a less viscous paste has higher tendency to be dispersed upon contact with water, body fluid or blood. The dispersion of the paste into its original powder form may cause various clinical complications, such as cement embolism.

SUMMARY OF THE INVENTION

A primary objective of the present invention is to provide a calcium-based bone cement composition with enhanced non-dispersive ability.

It is discovered that adding a very small amount of poly(acrylic acid) in the calcium-based bone cement can dramatically lower the possibility/risk of dispersion of the resulting cement paste. In other words, with addition of a small amount of poly(acrylic acid), the cement paste can tolerate a more dilute (higher L/P ratio) paste, which can be more easily delivered minimally invasively, without worrying about its being dispersed when injected into a bone cavity or other types of implantation site.

The embodiments of the present invention provides methods for providing a bone cement formula, bone cement paste, hardened bone cement composite, hardened bone cement composite with enhanced strength, and porous hardened bone cement composite.

An embodiment of the present invention provides a method for filling a hole or cavity in a bone with an exemplary embodiment of bone cement paste which will cure or harden in a hole or cavity in need of treatment.

Another embodiment of the present invention provides a method for implanting hardened bone cement composite during a treatment.

One embodiment of the present invention provides a calcium-based bone cement formula comprising a powder component and a setting liquid component with a liquid to powder ratio of 0.20 ml/g to 0.50 ml/g, preferably 0.25 ml/g to 0.45 m/g, wherein the powder component comprises a calcium phosphate source and the calcium phosphate source comprises tetracalcium phosphate (TTCP), characterized in that the bone cement formula further comprises, based on the total weight of the bone cement formula, 0.01-1%, preferably 0.03-0.5%, of poly(acrylic acid) having a repeating unit of —($CH_2$—C(COOH)H)n-, wherein n=50-50000, preferably 1000-5000, and more preferably 1500-2500.

Preferably, the poly(acrylic acid) is liquid, and is contained in the setting liquid component. Alternatively, the poly(acrylic acid) is solid, which can be powder, and contained in the powder component or dissolved in the setting liquid component prior to mixing the powder component and the setting liquid component.

In one embodiment, the powder component further comprises 5-65% of a calcium sulfate source, based on the total weight of the calcium sulfate source and the calcium phosphate source powder. The calcium sulfate source is calcium sulfate hemihydrate (CSH), calcium sulfate dehydrate (CSD), or anhydrous calcium sulfate, and preferably, CSH. The calcium phosphate source, in one aspect, further includes dicalcium phosphate, preferably dicalcium phosphate anhdydrous (DCPA), in a molar ratio of TTCP to dicalcium phosphate of approximately 0.5 to 2.5, preferably about 08 to 2.0, and more preferably about 1.0.

In one embodiment, the setting liquid component comprises ammonium ion ($NH_4^+$) in a concentration of about 0.075 M to 3.0 M.

The setting liquid component, in one example, is a solution of $NH_4H_2PO_4$, $(NH_4)_2HPO_4$, $(NH_4)_3PO_4 \cdot 3H_2O$, $(NH_4)_3PO_4$ or a mixture of them. Preferably, the setting liquid component is a solution of $(NH_4)_2HPO_4$. Preferably, the setting liquid component is an aqueous solution.

In one embodiment, the bone cement formula further comprises, based on the total weight of the powder component, 0.1-5%, preferably 0.25-5%, of a magnesium setting modifier selected from an oxide, hydroxide, fluoride, chloride, carbonate, phosphate, sulfate and silicate of magnesium. Preferably, the magnesium setting modifier is an oxide, phosphate or sulfate of magnesium, and more preferably, magnesium sulfate.

Additional features and benefits of the present invention will become apparent from the detailed description, figures and claims set forth below.

(abbreviated as PAA), and (b) is with an addition of 3 vol % PAA according to the present invention, respectively.

Figure 4:
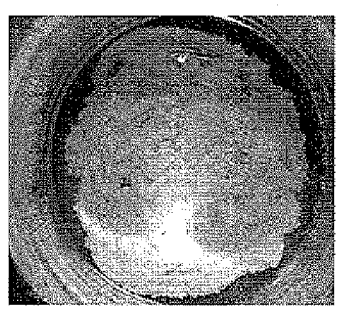
Figure 4:
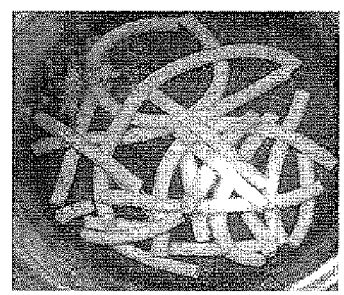

FIGS. 4 (a) and (b) are photographs showing green bodies of bone cement pastes (TTCP/DCPA:CSH=45/55, 0.60 M $(NH_4)_2HPO_4$, L/P=0.33 cc/g) injected into Hanks' solution, wherein (a) is without an addition of poly(acrylic acid) (abbreviated as FAA), and (b) is with an addition of 3 vol % PAA according to the present invention, respectively.

DETAILED DESCRIPTION OF THE INVENTION

Embodiment(s) of the present invention is a calcium-based bone cement formula with an enhanced non-dispersive ability, which is applicable to various medical fields, such as orthopedic, spinal, and dental surgeries. The calcium-based bone cement formula of the present invention has convenient working time and setting time to form a hardened block with high strength, excellent biocompatibility and superior osteoconductivity.

A process for preparing bone cement paste, in one embodiment, comprises mixing powder component with setting liquid component by a mixing mechanism such as agitation. The powder component, for example, may include mixture of calcium sulfate source and calcium phosphate source. Alternatively, calcium sulfate source and calcium phosphate source can be separate powders. In this case, calcium sulfate source and calcium phosphate source are combined first to form a power mixture prior to mixing with setting liquid component.

The calcium sulfate source and calcium phosphate source discussed earlier can be tetracalcium phosphate (TTCP) and/or dicalcium phosphate anhydrous (DCPA) powders. It should be noted that other types of sources can be used as long as they have similar chemical properties or characteristics as TTCP and/or DCPA.

The bone cement paste, in one embodiment, becomes hard or cured within a period of setting time under an atmosphere environment or an environment surrounded by body fluid such as blood. During an operation, an operator or doctor places bone cement paste into a hole or cavity at a damaged bone via a suitable tool through an incision. For example, for an orthopedic, spinal or root canal treatment, when bone cement paste becomes or cures into hardened bone cement composite in-situ, the hardened bone cement will be resorbed by the subject body over time in accordance with a predefined bioresorption rate.

The bone cement paste, in one embodiment, can be injected into a bone hole or cavity through a thin tube or with an orthopedic paste delivering tool such as a conventional medical instrument described in U.S. Pat. No. 7,325,702 B2, in which the paste will form a block of hardened bone cement. It should be noted that an orthopedic delivering tool is able to continually deliver the paste into a bone cavity until the cavity is filled.

The following examples via experimental procedures are illustrative and are intended to demonstrate embodiments of the present invention, which, however, should not be taken to limit the embodiments of the invention to the specific embodiments, but are for explanation and understanding only, since numerous modifications and variations will be apparent to those skilled persons in this art.

EXPERIMENTAL PROCEDURES

Abbreviation

TTCP: tetracalcium phosphate
DCPA: dicalcium phosphate anhydrous
CSH: calcium sulfate hemihydrate
WT: Working time
ST: Setting time
L/P ratio: Liquid/powder ratio
Chemicals Used for the Study

| Chemical | Formula | Manufacturer | Location |
|---|---|---|---|
| Tetracalcium phosphate (TTCP) | $Ca_4(PO_4)_2O$ | Fabricated in-house | Taiwan |
| Dicalcium phosphate anhydrous (DCPA) | $CaHPO_4$ | ACROS | New jersey, USA |
| Calcium sulfate hemihydrate (CSH) | $CaSO_4 \cdot \frac{1}{2}H_2O$ | Showa | Tokyo, Japan |
| Diammonium hydrogen phosphate | $(NH_4)_2HPO_4$ | Showa | Tokyo, Japan |
| Poly(acrylic acid) | $-(CH_2-C(COOH)H)_n-$ | Showa | Tokyo, Japan |

Preparation of TTCP Powder

The TTCP powder was fabricated in-house from the reaction of dicalcium pyrophosphate ($Ca_2P_2O_7$) (Sigma Chem. Co., St. Louis, Mo., USA) and calcium carbonate ($CaCO_3$) (Katayama Chem. Co., Tokyo, Japan) using the method suggested by Brown and Epstein [*Journal of Research of the National Bureau of Standards—A Physics and Chemistry* 6 (1965) 69A 12].

TTCP powder was prepared by mixing $Ca_2P_2O_7$ powder with $CaCO_3$ powder uniformly for 12 hours. The mixing ratio of $Ca_2P_2O_7$ powder to $CaCO_3$ powder was 1:1.27 (weight ratio) and the powder mixture was heated to 1400° C. to allow two powders to react to form TTCP.

Preparation of a TTCP/DCPA/CSH Composite Paste

Appropriate amounts of TTCP and DCPA powders were uniformly mixed in a ball miller, followed by uniformly mixing with appropriate amount of CSH powder. The resultant TTCP/DCPA/CSH mixed powders were mixed uniformly with a desirable setting solution (e.g., 0.6M $(NH_4)_2HPO_4$) at a desirable LAP ratio (e.g., 0.28 ml/g) to form a TTCP/DCPA/CSH paste.

Preparations of TTCP/DCPA, TTCP/CSH and TTCP/DCPA:CSH Powder Components

Appropriate amounts of TTCP and CSH powders were uniformly mixed in a ball miller to obtain a powder component of TTCP/CSH. TTCP and DCPA powders were uniformly mixed in a ball miller in a molar ratio of 1:1 to obtain a powder component of TTCP/DCPA. Appropriate amounts of the resulting TTCP/DCPA mixed powder and CSH powder were uniformly mixed in a ball miller to obtain a powder component of TTCP/DCPA:CSH. The weight ratios of TTCP, DCPA and CSH of the TTCP/DCPA:CSH powder components used in following examples of the present application are listed as follows, wherein TTCP and DCPA mixed are in a molar ratio of 1:1:

| TTCP/DCPA:CSH (by weight) | TTCP:DCPA:CSH (by weight) |
|---|---|
| 90:10 | 2.69:1:0.41 |
| 85:15 | 2.69:1:0.65 |
| 80:20 | 2.69:1:0.92 |
| 75:25 | 2.69:1:1.23 |
| 65:35 | 2.69:1:1.99 |
| 55:45 | 2.69:1:3.02 |
| 45:55 | 2.69:1:4.51 |
| 35:65 | 2.69:1:6.85 |
| 25:75 | 2.69:1:11.07 |
| 10:90 | 2.69:1:33.21 |

Preparations of Setting Liquid Components

Poly(acrylic acid) (abbreviated as PAA) has a molecular weight of 150,000 and was obtained as 25 wt % aqueous solution (reagent grade, Showa, Japan). Diammonium hydrogen phosphate [$(NH_4)_2HPO_4$] solutions of different concentrations were used to prepare $(NH_4)_2HPO_4$ solutions having different volume percentages of the PAA aqueous solution by mixing the $(NH_4)_2HPO_4$ solutions separately with the PAA aqueous solution as-received in different volume ratios, expressed as "PAA conc in setting soln (vol %)" in the Tables of the following examples.

Working Time/Setting Time Measurement

The working time of cement paste was determined by the time after that the cement paste was no longer workable. The setting time of cement paste was measured according to the standard method set forth in ISO 1566 for dental zinc phosphate cements. The cement is considered set when a 400 gm weight loaded onto a Vicat needle with a 1 mm diameter tip fails to make a perceptible circular indentation on the surface of the cement.

Dispersion Behavior Evaluation

A cement paste was prepared by mixing a powder component and a setting liquid component with a desired liquid to powder ratio (ml/g) for one minute, and then the paste was immediately injected into a Hanks' solution bath at 37° C. via a 5 ml syringe. The injected cement paste green body in the Hanks' solution was observed to determine its dispersion behavior.

Severity Level of Dispersion Upon Contact with Water:

1—Negligible
2—Mild
3—Extensive
4—Extremely severe

Example 1. Effect of PAA Concentration on Dispersion Behavior and Working/Setting Time of "65:35" Composite Cement Paste Prepared from 0.45 M $(NH_4)_2HPO_4$ Setting Solution with L/P Ratio of 0.35 ml/g A cement paste was prepared by mixing the TTCP/DCPA:CSH=65:35 powder component with 0.45 M $(NH_4)_2HPO_4$ setting solution containing various volume percentages of PAA and with a L/P ratio of 0.35 ml/g, and dispersion behavior and working/setting time of the resulting paste were evaluated. The results and the contents of PAA are listed in the following Table 1.

TABLE 1

TTCP/DCPA:CSH = 65:35, 0.45M $(NH_4)_2HPO_4$, L/P ratio of 0.35 ml/g

| Powder | PAA conc in setting soln (vol %) | PAA conc in paste (wt %)* | WT/ST (Min) | Severity index of paste dispersion |
|---|---|---|---|---|
| 65:35 | — | 0 | 11.5/13.3 | 3 |
| 65:35 | 0.25 | 0.018 | 11.4/13.8 | 2 |
| 65:35 | 0.5 | 0.036 | 11.2/14.4 | 1 |
| 65:35 | 5.0 | 0.355 | 9.4/13.0 | 1 |
| 65:35 | 7.0 | 0.497 | 9.3/12.8 | 1 |
| 65:35 | 10.0 | 0.709 | 9.2/13.1 | 1 |

*PAA conc in paste (wt %): percentage of PAA based on the total weight of the cement paste Results:
(1) The severity of cement paste dispersion in water dramatically decreases as small amounts of PAA are introduced into the formula.
(2) WT/ST significantly decreases as PAA concentration>5 vol % in solution.

Example 2. Effect of PAA Concentration on Dispersion Behavior and Working/Setting Time of "65:35" Composite Cement Paste Prepared from 0.45 M $(NH_4)_2HPO_4$ Setting Solution with L/P Ratio of 0.30 ml/g This example was conducted similarly as in Example 1 except that L/P ratio was changed from 0.35 ml/g to 0.30 ml/g. The results and the contents of PAA are listed in the following Table 2.

TABLE 2

TTCP/DCPA:CSH = 65:35, 0.45M $(NH_4)_2HPO_4$, L/P ratio of 0.30 ml/g

| Powder | PAA conc in setting soln (vol %) | PAA conc in paste (wt %)* | WT/ST (Min) | Severity index of paste dispersion |
|---|---|---|---|---|
| 65:35 | — | 0 | 10.3/12.8 | 4[a] |
| 65:35 | 0.5 | 0.032 | 9.5/11.9 | 2 |
| 65:35 | 1.0 | 0.063 | 9.5/11.9 | 1[b] |
| 65:35 | 3.0 | 0.190 | 6.7/8.7 | 1 |
| 65:35 | 5.0 | 0.316 | 6.5/8.5 | 1 |

Figure 1:
FIGS. 1 (a) and (b) are photographs showing green bodies of bone cement pastes (TTCP/DCPA:CSH=65/35, 0.45 M $(NH_4)_2HPO_4$, L/P=0.30 cc/g) injected into Hanks' solution, wherein (a) is without an addition of poly(acrylic acid) (abbreviated as PAA), and (b) is with an addition of 3 vol % PAA according to the present invention, respectively.
Figure 1:
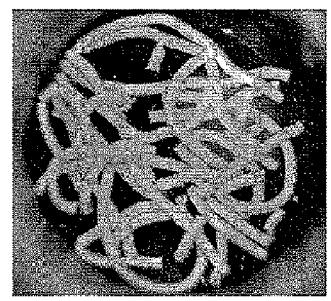

*same as in Table 1.
[a],[b]Photographs of the injected green bodies of the cement pastes in Hanks' solution are shown in FIG. 1 (a) and (b), respectively.

Results:
(1) The severity of cement paste dispersion in water dramatically decreases as small amounts of PAA are introduced into the formula.
(2) WT/ST significantly decreases as PAA concentration>3 vol % in solution.

Example 3. Effect of PAA Concentration on Dispersion Behavior and Working/Setting Time of "65:35" Composite Cement Paste Prepared from 0.60 M $(NH_4)_2HPO_4$ Setting Solution with L/P Ratio of 0.33 ml/g A cement paste was prepared by mixing the TTCP/DCPA:CSH=65:35 powder component with 0.60 M $(NH_4)_2HPO_4$ setting solution containing 3 vol % of PAA with a L/P ratio of 0.33 ml/g, and dispersion behavior and working/setting time of the resulting paste were evaluated. In this example, some of the cement pastes prepared were added with a magnesium-containing compound, which was added to the powder component prior to mixing with the setting solution.

$MgSO_4$ purchased from Showa (Japan) was ground and filtered with a sieve with a mesh number of 200, so that sizes of the particles were controlled at about 0.074 mm.

MgO purchased from Showa (Japan) was ground by ball milling with two times of the weight of the MgO of alumina milling balls (diameter of 10 mm) in a 500 ml plastic bottle for two hours.

$Mg_3(PO_4)_2$ was prepared by heating $Mg_3P_2O_8\cdot 8H_2O$ purchased from Sigma-Aldrich (Germany) in an oven at 500° C. for three hours to remove the crystalline water.

For the cement pastes further containing a magnesium-containing compound, 30 g of the TTCP/DCPA:CSH=65:35 powder component, 60 g of alumina milling balls (diameter of 10 mm), and a desired amount of the powder of the magnesium-containing compound were added into a 500 ml plastic bottle, and the resulting mixture was ball milled for one day.

The results and the contents of PAA are listed in the following Table 3.

TABLE 3

TTCP/DCPA:CSH = 65:35, 0.60M (NH$_4$)$_2$HPO$_4$, L/P ratio of 0.33 ml/g

| Powder | PAA conc in setting soln (vol %) | PAA conc in paste (wt %)* | WT/ST (Min) | Severity index of paste dispersion |
|---|---|---|---|---|
| 65:35 | — | 0 | 8.5/10.3 | 3[a] |
| 65:35 | 3.0 | 0.203 | 6.0/7.9 | 1[b] |
| 65:35 + 0.25% MgSO$_4$ | 3.0 | 0.203 | 15.4/17.7 | 1 |
| 65:35 + 0.5% MgSO$_4$ | 3.0 | 0.203 | 14.7/17.0 | 1 |
| 65:35 + 1% MgSO$_4$ | 3.0 | 0.203 | 14.4/16.5 | 1 |
| 65:35 + 0.5% Mg$_3$(PO$_4$)$_2$ | 3.0 | 0.203 | 5.9/8.2 | 1 |
| 65:35 + 1.0% Mg$_3$(PO$_4$)$_2$ | 3.0 | 0.203 | 13.8/16.1 | 1 |
| 65:35 + 0.5% MgO | 3.0 | 0.203 | 11.5/13.9 | 1 |
| 65:35 + 1.0% MgO | 3.0 | 0.203 | 11.7/14.3 | 1 |

Figure 2:
FIGS. 2 (a) and (b) are photographs showing green bodies of bone cement pastes (TTCP/DCPA:CSH=65/35, 0.60 M $(NH_4)_2HPO_4$, L/P=0.33 cc/g) injected into Hanks' solution, wherein (a) is without an addition of poly(acrylic acid) (abbreviated as PAA), and (b) is with an addition of 3 vol % FAA according to the present invention, respectively.
Figure 2:
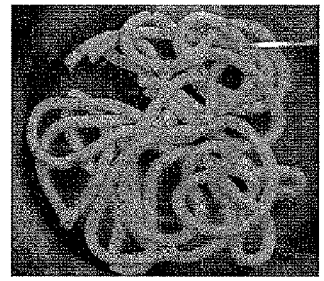

*same as in Table 1.
[a],[b]Photographs of the injected green bodies of the cement pastes in Hanks' solution are shown in FIG. 2 (a) and (b), respectively.

Results:
(1) The severity of cement paste dispersion in water dramatically decreases as small amounts of PAA are introduced into the formula.
(2) WT/ST significantly decreases as PAA concentration>3 vol % in solution.
(3) As small amounts of MgSO$_4$, Mg$_3$(PO$_4$)$_2$ or MgO are further added, the PAA-induced decrease in WT/ST is recovered.

Example 4. Effect of PAA Concentration on Dispersion Behavior and Working/Setting Time of "65:35", "35:65" and "45:55" Composite Cement Pastes Prepared from 0.60 M (NH$_4$)$_2$HPO$_4$ Setting Solution with L/P Ratios of 0.30, 0.33 and 35 ml/g In this example the cement pastes were prepared with 0.60 M (NH$_4$)$_2$HPO$_4$ setting solution and various powder components, and L/P ratios as indicated in the following Table 4, wherein the severity index of paste dispersion is for each cement paste is also listed.

TABLE 4

TTCP/DCPA:CSH = 65:35, 35:65 and 45:55, 0.60M (NH$_4$)$_2$HPO$_4$, L/P ratios of 0.30, 0.33 and 35 ml/g

| Powder | PAA conc in setting soln (vol %) | PAA conc in paste (wt %)* | L/P (ml/g) | WT/ST (Min) | Severity index* of paste dispersion |
|---|---|---|---|---|---|
| 65:35 | — | 0 | 0.30 | 8.5/10.3 | 3 |
| 65:35 | 3.0 | 0.189 | 0.30 | 5.7/7.2 | 1 |
| 35:65 | — | | 0.35 | 8.4/9.3 | 3[a] |
| 35:65 | 0.5 | 0.035 | 0.35 | 9.0/10.5 | 2 |
| 35:65 | 1.0 | 0.071 | 0.35 | 9.4/10.3 | 2 |
| 35:65 | 3.0 | 0.212 | 0.35 | 10.5/11.2 | 1[b] |
| 35:65 | — | | 0.33 | 7.8/8.8 | 4 |
| 35:65 | 3.0 | 0.203 | 0.33 | 7.5/8.8 | 1 |
| 45:55 | — | | 0.35 | 10.5/12.8 | 4 |
| 45:55 | 1.0 | 0.071 | 0.35 | 10.9/13.0 | 2 |

TABLE 4-continued

TTCP/DCPA:CSH = 65:35, 35:65 and 45:55, 0.60M (NH$_4$)$_2$HPO$_4$, L/P ratios of 0.30, 0.33 and 35 ml/g

| Powder | PAA conc in setting soln (vol %) | PAA conc in paste (wt %)* | L/P (ml/g) | WT/ST (Min) | Severity index* of paste dispersion |
|---|---|---|---|---|---|
| 45:55 | 3.0 | 0.212 | 0.35 | 4.2/6.5 | 1 |
| 45:55 | — | | 0.30 | 5.8/7.9 | 4 |
| 45:55 | 1.0 | 0.063 | 0.30 | 6.3/8.5 | 2 |
| 45:55 | 3.0 | 0.189 | 0.30 | 4.0/6.4 | 1 |

Figure 3:
FIGS. 3 (a) and (b) are photographs showing green bodies of bone cement pastes (TTCP/DCPA:CSH=35/65, 0.60 M $(NH_4)_2HPO_4$, L/P=0.33 cc/g) injected into Hanks' solution, wherein (a) is without an addition of poly(acrylic acid)
Figure 3:
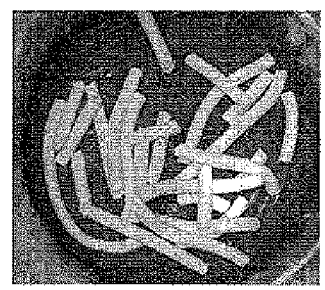

*Same as in Table 1
[a],[b]Photographs of the injected green bodies of the cement pastes in Hanks' solution are shown in FIG. 3 (a) and (b), respectively.

Results:
(1) The severity of cement paste dispersion in water dramatically decreases as small amounts of PAA are introduced into the formula.

Example 5. Effect of PAA Concentration on Dispersion Behavior and Working/Setting Time of "45:55" Composite Cement Paste Prepared from 0.60 M (NH$_4$)$_2$HPO$_4$ Setting Solution with L/P Ratio of 0.33 ml/g In this example some of the cement pastes prepared were added with a magnesium-containing compound similarly as in Example 3.

TABLE 5

TTCP/DCPA:CSH = 45:55, 0.60M (NH$_4$)$_2$HPO$_4$, L/P ratio of 0.33 ml/g

| Powder | PAA conc in setting soln (vol %) | PAA conc in paste (wt %)* | WT/ST (Min) | Severity index* of paste dispersion |
|---|---|---|---|---|
| 45:55 | — | 0 | 8.8/10.5 | 4[a] |
| 45:55 | 1.0 | 0.068 | 9.7/11.8 | 2 |
| 45:55 | 3.0 | 0.203 | 4.1/6.2 | 1[b] |
| 45:55 + 0.5% MgSO$_4$ | 3.0 | 0.203 | 15.7/18.3 | 1 |
| 45:55 + 1.0% MgSO$_4$ | 3.0 | 0.203 | 11.3/13.5 | 1 |
| 45:55 + 0.5% Mg$_3$(PO$_4$)$_2$ | 3.0 | 0.203 | 14.3/16.5 | 1 |
| 45:55 + 0.5% MgO | 3.0 | 0.203 | 11.5/14.5 | 1 |

*Same as in Table 1
[a],[b]Photographs of the injected green bodies of the cement pastes in Hanks' solution are shown in FIG. 4 (a) and (b), respectively.

Results:
(1) The severity of cement paste dispersion in water dramatically decreases as small amounts of PAA are introduced into the formula.
(2) WT/ST significantly decreases as PAA concentration>3 vol % in solution.
(3) As small amounts of MgSO$_4$, Mg$_3$(PO$_4$)$_2$ or MgO are further added, the PAA-induced decrease in WT/ST is recovered.

Example 6. Effect of PAA Concentration on Dispersion Behavior and Working/Setting Time of "85:15" Composite Cement Paste Prepared from 0.0375 M (NH$_4$)$_2$HPO$_4$ Setting Solution with L/P Ratio of 0.25 ml/g In this example a setting solution of 0.0375 M (NH$_4$)$_2$HPO$_4$ containing 1 vol % of PAA was used to evaluate the effect on the dispersion behavior. The conditions and results are listed in the following Table 6.

TABLE 6

TTCP/DCPA:CSH = 85:15, 0.0375M (NH$_4$)$_2$HPO$_4$, L/P ratio of 0.25 ml/g

| Powder | PAA conc in setting soln (vol %) | PAA conc in paste (wt %)* | WT/ST (Min) | Severity index* of paste dispersion |
|---|---|---|---|---|
| 85/15 | — | 0 | — | 4 |
| 85/15 | 1.0 | 0.056 | — | 2 |

*Same as in Table 1

Results:

(1) The severity of cement paste dispersion in water dramatically decreases as a small amount of PAA is introduced into the formula.

Example 7. Effect of PAA Concentration on Dispersion Behavior and Working/Setting Time of "TTCP/DCPA" Cement Paste Prepared from 0.0375M (NH$_4$)$_2$HPO$_4$ Setting Solution In this example setting solutions of 0.0375 M (NH$_4$)$_2$HPO$_4$ containing small amounts of PAA were used to evaluate the effect on the dispersion behavior. The conditions and results are listed in the following Table 7.

TABLE 7

TTCP/DCPA = 1:1 (mole), 0.0375M (NH$_4$)$_2$HPO$_4$

| TTCP/ DCPA Powder | PAA conc in setting soln (vol %) | PAA conc in paste (wt %)* | L/P (ml/g) | WT/ST (Min) | Severity index* of paste dispersion |
|---|---|---|---|---|---|
| 1:1 (mole) | — | 0 | 0.28 | 10.4/13.0 | 3 |
| 1:1 (mole) | 0.5 | 0.030 | 0.28 | 9.4/11.0 | 2 |
| 1:1 (mole) | 2.0 | 0.121 | 0.28 | 8.6/9.9 | 1 |
| 1:1 (mole) | — | — | 0.26 | 10.1/12.2 | 3 |
| 1:1 (mole) | 0.5 | 0.029 | 0.26 | 8.3/9.6 | 2 |
| 1:1 (mole) | 1.0 | 0.057 | 0.26 | 7.7/9.3 | 1 |
| 1:1 (mole) | — | — | 0.24 | 6.7/8.0 | 4 |
| 1:1 (mole) | 0.5 | 0.027 | 0.24 | 5.2/6.6 | 2 |
| 1:1 (mole) | 1.0 | 0.054 | 0.24 | 5.4/6.6 | 2 |

*Same as in Table 1

Results:

(1) The severity of cement paste dispersion in water dramatically decreases as small amounts of PAA are introduced into the formula.

Example 8. Effect of PAA Concentration on Dispersion Behavior of TTCP/CSH=45:35 Cement Paste Prepared from 0.45 M and 0.60 M (NH$_4$)$_2$HPO$_4$ Setting Solutions with L/P Ratios of 0.35 and 0.30 ml/g TTCP powder and CSH powder were mixed thoroughly in a ratio of 45:35 by weight, and to the resulting powder mixture (NH$_4$)$_2$HPO$_4$ setting solutions containing various volume percentages of PAA were added according to L/P ratios as listed in the following Table 8. The dispersion behavior of the resulting pastes were evaluated. The conditions and results are listed in the following Table 8.

TABLE 8

TTCP/CSH = 45:35, 0.45M and 0.60M (NH$_4$)$_2$HPO$_4$, L/P ratios of 0.35 and 0.30 ml/g

| TTCP:CSH | (NH$_4$)$_2$HPO$_4$ (M) | PAA conc in setting soln (vol %) | PAA conc in paste (wt %) | L/P ratio (ml/g) | Severity index* of paste dispersion |
|---|---|---|---|---|---|
| 45:55 | 0.45 | — | 0 | 0.35 | 4 |
| 45:55 | 0.45 | 1.0 | 0.071 | 0.35 | 1 |
| 45:55 | 0.45 | 3.0 | 0.213 | 0.35 | 1 |
| 45:55 | 0.45 | — | 0 | 0.35 | 4 |
| 45:55 | 0.45 | 3.0 | 0.190 | 0.30 | 1 |
| 45:55 | 0.60 | — | 0 | 0.30 | 4 |
| 45:55 | 0.60 | 3.0 | 0.189 | 0.30 | 1 |

*Same as in Table 1

Results:

(1) The severity of cement paste dispersion in water dramatically decreases as small amounts of PAA are introduced into the formula.

Example 9. Effect of PAA Concentration on Dispersion Behavior and Working/Setting Time of "TTCP" Cement Paste Prepared from 0.0375M (NH$_4$)$_2$HPO$_4$ Setting Solution with L/P Ratio of 0.33 ml/g TTCP powder and 0.0375 (NH$_4$)$_2$HPO$_4$ setting solution containing various volume percentages of PAA were mixed with a L/P ratio of 0.33. The dispersion behavior and working/setting time of the resulting pastes were evaluated. The conditions and results are listed in the following Table 9.

TABLE 9

TTCP, 0.0375M (NH$_4$)$_2$HPO$_4$, L/P ratio of 0.33 ml/g

| Powder | PAA conc in setting soln (vol %) | PAA conc in paste (wt %) | WT/ST (Min) | Severity index* of paste dispersion |
|---|---|---|---|---|
| TTCP | — | 0 | 6.6/7.9 | 4 |
| TTCP | 2.0 | 0.138 | 6.3/7.7 | 3 |
| TTCP | 5.0 | 0.344 | — | 2 |

Results:

(1) The severity of cement paste dispersion in water dramatically decreases as small amounts of PAA are introduced into the formula.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

The invention claimed is:

1. A hardened block of a calcium-based bone cement formula consisting of a powder component, a liquid solution with a liquid to powder ratio of 0.20 ml/g to 0.50 ml/g, and, based on the total weight of the bone cement formula, 0.01-1% of poly(acrylic acid) having a repeating unit of —(CH2-C(COOH)H)n-, wherein n=50-50000, wherein the powder component consists of tetracalcium phosphate (TTCP) and dicalcium phosphate, or the powder component consists of TTCP, dicalcium phosphate and a calcium sulfate source, wherein a molar ratio of the TTCP to the dicalcium phosphate is of about 0.5 to about 2.5, and a content of the calcium sulfate source is of 5-65%, based on the total weight of the TTCP, dicalcium phosphate and the calcium phosphate source, and wherein the calcium sulfate source is calcium sulfate hemihydrate (CSH), calcium sulfate dehydrate (CSD), or anhydrous calcium sulfate, wherein the liquid solution comprises ammonium ion ($NH_4^+$) in a concentration of about 0.075 M to 3 M, and wherein the liquid solution is a solution of $NH_4H_2PO_4$, $(NH_4)_2HPO_4$, $(NH_4)_3PO_4 \cdot 3H_2O$, $(NH_4)_3PO_4$, or a mixture solution of two or more of $NH_4H_2PO_4$, $(NH_4)_2HPO_4$, $(NH_4)_3PO_4 \cdot 3H_2O$, and $(NH_4)_3PO_4$.

2. The hardened block of bone cement formula of claim 1, wherein n=1000-5000.

3. The hardened block of bone cement formula of claim 1, wherein n=1500-2500.

4. The hardened block of bone cement formula of claim 1, wherein the dicalcium phosphate is dicalcium phosphate anhdydrous (DCPA).

5. The hardened block of bone cement formula of claim 1, wherein the molar ratio of TTCP to dicalcium phosphate is about 1.0.

6. The hardened block of bone cement formula of claim 1, wherein the liquid solution is a solution of $(NH_4)_2HPO_4$.

* * * * *